(12) United States Patent
Park et al.

(10) Patent No.: US 10,993,691 B2
(45) Date of Patent: May 4, 2021

(54) APPARATUS AND METHOD FOR REARRANGING PROTOCOLS IN RADIOGRAPHY SYSTEM

(71) Applicant: Samsung Electronics Co., Ltd., Gyeonggi-do (KR)

(72) Inventors: Seolynn Park, Seoul (KR); Eunmee Shin, Gyeonggi-do (KR); Miyoung Lee, Seoul (KR); Gukho Gil, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 93 days.

(21) Appl. No.: 16/345,342

(22) PCT Filed: Oct. 24, 2017

(86) PCT No.: PCT/KR2017/011759
§ 371 (c)(1),
(2) Date: Apr. 26, 2019

(87) PCT Pub. No.: WO2018/080131
PCT Pub. Date: May 3, 2018

(65) Prior Publication Data
US 2019/0313996 A1 Oct. 17, 2019

(30) Foreign Application Priority Data
Oct. 28, 2016 (KR) ........................ 10-2016-0141960

(51) Int. Cl.
*H05G 1/64* (2006.01)
*A61B 6/00* (2006.01)
*H04L 29/08* (2006.01)

(52) U.S. Cl.
CPC .............. *A61B 6/545* (2013.01); *A61B 6/465* (2013.01); *A61B 6/5294* (2013.01); *H04L 67/12* (2013.01)

(58) Field of Classification Search
CPC ....... A61B 6/032; A61B 6/4405; A61B 6/465; A61B 6/5294; A61B 6/545; A61B 6/563;
(Continued)

(56) References Cited

U.S. PATENT DOCUMENTS

2006/0242095 A1 10/2006 Takada et al.
2012/0189180 A1 7/2012 Yeluri et al.
(Continued)

FOREIGN PATENT DOCUMENTS

JP 2000-166908 A 6/2000
JP 2006-231040 A 9/2006
(Continued)

*Primary Examiner* — Irakli Kiknadze
(74) *Attorney, Agent, or Firm* — Cha & Reiter, LLC.

(57) ABSTRACT

Various embodiments of the present invention relate to an apparatus for rearranging protocols in an electronic device, and an operating method therefor. The electronic device comprises: a transceiver unit; and at least one processor functionally coupled to the transceiver unit, wherein the at least one processor is configured to: control an operation of receiving information on a first protocol list including a plurality of protocols from a server; identify, for each of the plurality of protocols, position information of a radiography apparatus which captures an image, and the type of detection unit which detects a beam generated from the radiophotography apparatus; rearrange the order of the plurality of protocols on the basis of at least one of the position information of the radiography apparatus and the type of detection unit, so as to generate a second protocol list; and control an operation of transmitting information on the second protocol list to the radiography apparatus.

14 Claims, 13 Drawing Sheets

(58) Field of Classification Search
CPC ..... A61B 6/4283; A61B 6/461; A61B 6/4411; A61B 6/4233; A61B 6/4494; A61B 6/54; A61B 6/548; A61B 6/566; A61B 6/42; A61B 6/4208; A61B 6/4266; A61B 6/44; A61B 6/4452; A61B 6/4464; A61B 6/4476; A61B 6/46; A61B 5/7275; A61B 6/5217; A61B 5/7203; A61B 2576/02; A61B 5/0066; A61B 5/02416; A61B 5/7207; A61B 5/7264; A61B 5/0002; A61B 5/0205; A61B 5/055; A61B 5/4848; A61B 6/469; A61B 6/481; A61B 6/507; A61B 5/002; A61B 5/0088; A61B 5/08; A61B 6/542; A61B 6/467; A61B 2576/026; A61B 6/463; A61B 6/5205; A61B 6/5229; A61B 6/4435; A61B 6/488; A61B 6/5235; A61B 6/00; A61B 6/04; A61B 6/06; H04L 67/12; H04L 67/125; G01N 23/04; G16H 30/20; G16H 10/60; G16H 30/40; G16H 40/20; G16H 40/40; G16H 40/60; G16H 40/63; G16H 40/67; G16H 50/20; G16H 50/70; G16H 70/20; A61N 2005/007; A61N 2005/0626; A61N 2005/063; A61N 2005/0643; A61N 2005/0662; A61N 2005/0664; A61N 2005/0667; A61N 2005/067; A61N 5/0616; A61N 5/0625; G06N 20/00
USPC .................................................... 378/62, 98
See application file for complete search history.

(56) References Cited

U.S. PATENT DOCUMENTS

| | | |
|---|---|---|
| 2013/0038738 A1 | 2/2013 | Ando et al. |
| 2013/0336456 A1 | 12/2013 | Tanaka |
| 2014/0222444 A1* | 8/2014 | Cerello .................. G16H 15/00 705/2 |
| 2015/0063535 A1* | 3/2015 | Gatayama ............. A61B 6/469 378/19 |
| 2015/0091778 A1* | 4/2015 | Day ....................... G16H 30/40 345/1.3 |
| 2017/0103552 A1* | 4/2017 | Kim ....................... A61B 5/055 |
| 2017/0228857 A1* | 8/2017 | Carmi ................... G06T 7/0012 |

FOREIGN PATENT DOCUMENTS

| | | |
|---|---|---|
| JP | 2014-000131 A | 1/2014 |
| JP | 2016-22096 A | 2/2016 |
| JP | 2016-27888 A | 2/2016 |
| KR | 10-2015-0010515 A | 1/2015 |
| KR | 10-2015-0020946 A | 2/2015 |

\* cited by examiner

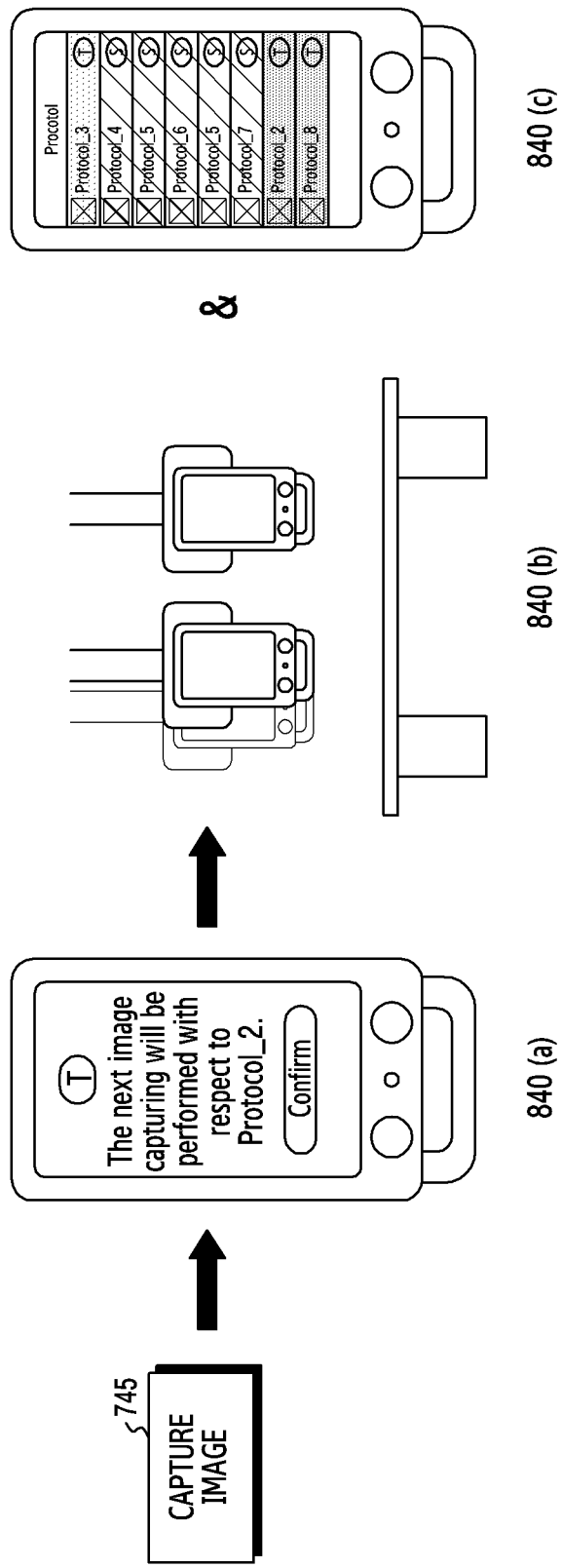

APPARATUS AND METHOD FOR REARRANGING PROTOCOLS IN RADIOGRAPHY SYSTEM

CLAIM OF PRIORITY

This application is a National Phase Entry of PCT International Application No. PCT/KR2017/011759, which was filed on Oct. 24, 2017, and claims a priority to Korean Patent Application No. 10-2016-0141960, which was filed on Oct. 28, 2016, the contents of which are incorporated herein by reference.

TECHNICAL FIELD

Various embodiments of the disclosure relate to a radiography system, and more particularly, to an apparatus and a method for rearranging protocols.

BACKGROUND ART

A radiography system refers to a system that obtains an image regarding an internal structure of an examinee by using a radiography device, and collects and manages various data regarding the obtained image by using an electronic device such as a work station. A doctor may output images obtained by the radiography system, and may diagnose a health condition and a disease of the examinee by analyzing the images. For example, an X-RAY device which is a kind of radiography system may grasp an internal structure (for example, a bone or etc.) of an object (for example, a patient or an examinee) by allowing an X-ray having a short wavelength to pass through the body.

A radiological technologist captures an image regarding the inside of the body of the examinee by using the radiography device, in consideration of an order of protocols transmitted from the doctor. In the disclosure, the protocol refers to an image capturing technique that the radiological technologist intends to use to capture an image by using the radiography device. In general, the list of protocols transmitted from the doctor does not consider a moving line of the radiography device or a moving line of the examinee. Therefore, the radiological technologist should rearrange the list of protocols to perform radiography efficiently. In addition, it may be difficult to identify a protocol for which image capturing has been already completed when radiography is performed based on the list of protocols transmitted from the doctor. Therefore, the radiological technologist is required to identify protocols that remain to perform image capturing.

DISCLOSURE OF INVENTION

Technical Problem

Based on the above-described discussion, various embodiments of the disclosure provide an apparatus and a method for minimizing a moving line of a radiography device and a moving line of an examinee by rearranging a list of protocols received from a doctor, based on a predefined classification criterion and/or an image-capturing pattern of a radiological technologist, and visualizing the rearranged list of protocols.

Solution to Problem

According to various embodiments of the disclosure, an operation method of an electronic device in a radiography system includes: receiving, from a server, information regarding a first protocol list including a plurality of protocols; identifying position information of a radiography device which performs image capturing with respect to each of the plurality of protocols, and a type of a detector which detects a beam generated from the radiography device; generating a second protocol list by rearranging the order of the plurality of protocols, based on at least one of the position information of the radiography device and the type of the detector; and transmitting information regarding the second protocol list to the radiography device, wherein the position information of the radiography device, and the type of the detector are determined based on an image capturing technique indicated by each of the plurality of protocols.

According to various embodiments of the disclosure, an operation method of a radiography device in a radiography system includes: receiving information regarding a second protocol list from an electronic device; and, based on an order of a plurality of protocols included in the second protocol list, performing image capturing with respect to each of the plurality of protocols, wherein the second protocol list is generated by rearranging an order of the plurality of protocols included in a first protocol list, and is generated based on at least one of position information of the radiography device regarding each of the plurality of protocols, and a type of a detector for detecting a beam generated from the radiography device, wherein the position information of the radiography device, and the type of the detector are determined based on an image capturing technique indicated by each of the plurality of protocols.

According to various embodiments of the disclosure, an electronic device in a radiography system includes: a transceiver; and at least one processor functionally coupled to the transceiver, wherein the at least one processor is configured to: control to receive, from a server, information regarding a first protocol list including a plurality of protocols; identify position information of a radiography device which performs image capturing with respect to each of the plurality of protocols, and a type of a detector which detects a beam generated from the radiography device; generate a second protocol list by rearranging the order of the plurality of protocols, based on at least one of the position information of the radiography device and the type of the detector, and control to transmit information regarding the second protocol list to the radiography device, wherein the position information of the radiography device, and the type of the detector are determined based on an image capturing technique indicated by each of the plurality of protocols.

According to various embodiments of the disclosure, a radiography device in a radiography system includes: a transceiver, and at least one processor functionally coupled to the transceiver, wherein the at least one processor is configured to: control to receive information regarding a second protocol list from an electronic device; and, based on an order of a plurality of protocols included in the second protocol list, perform image capturing with respect to each of the plurality of protocols, wherein the second protocol list is generated by rearranging, by the electronic device, an order of the plurality of protocols included in a first protocol list, and is generated based on at least one of position information of the radiography device regarding each of the plurality of protocols, and a type of a detector for detecting a beam generated from the radiography device, wherein the position information of the radiography device, and the type of the detector are determined based on an image capturing technique indicated by each of the plurality of protocols.

Advantageous Effects of Invention

The electronic device and the operation method thereof according to various embodiments of the disclosure can minimize a moving line of the radiography device and a motion line of an examinee by rearranging the order of protocols based on a predefined classification criterion and/or user pattern information.

The effects that can be achieved by the disclosure are not limited to the above-mentioned effects, and other effects that have not been mentioned can be clearly understood by a person skilled in the art based on the following descriptions.

BRIEF DESCRIPTION OF DRAWINGS

FIGS. 8A and 8B are views illustrating an example of an operation automatically performing image capturing.

BEST MODE FOR CARRYING OUT THE INVENTION

Figure 1:
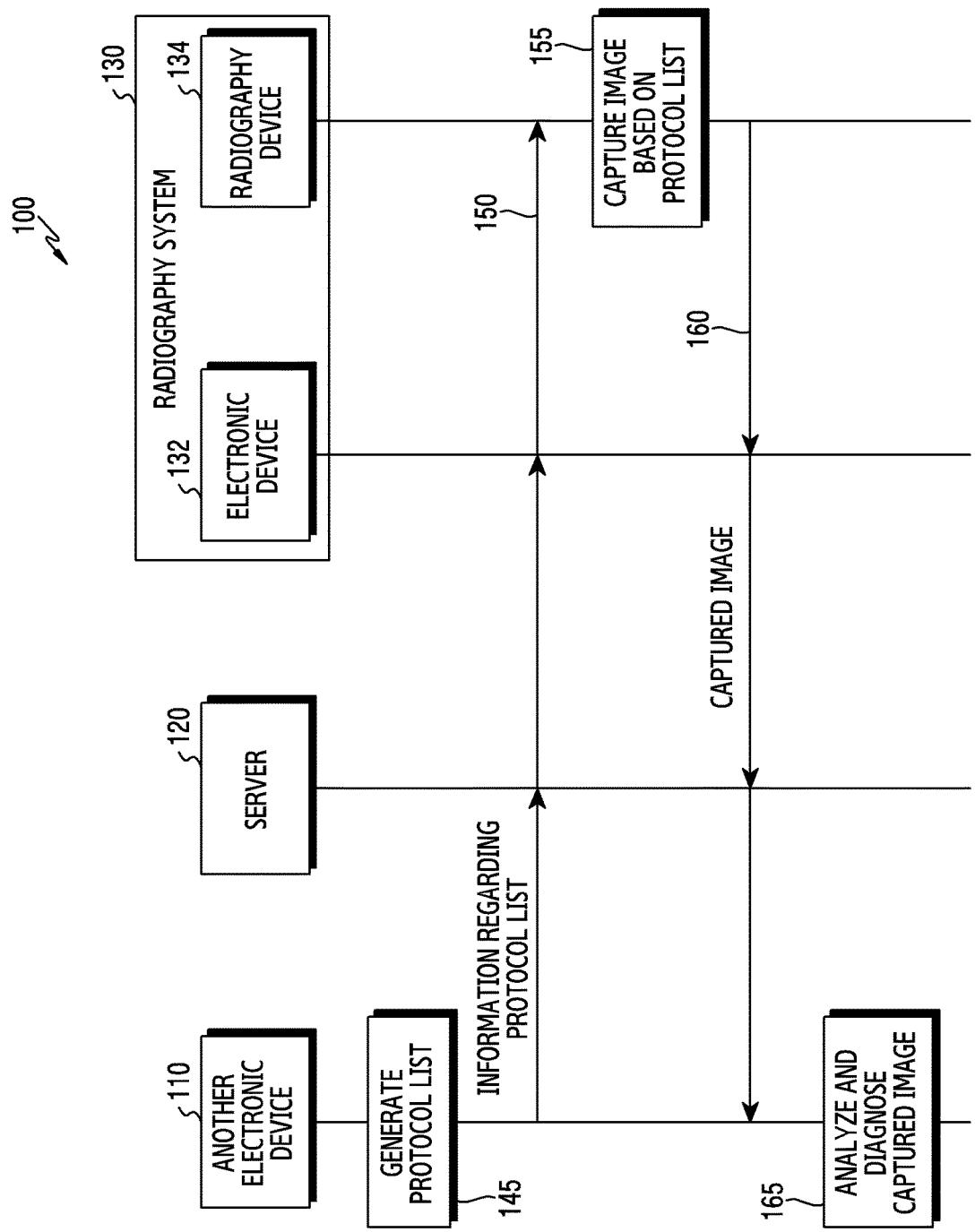
FIG. 1 is a view illustrating a network environment including a radiography system according to various embodiments.

Hereinafter, various embodiments of the disclosure will be described with reference to the accompanying drawings. It should be appreciated that various embodiments and the terms used therein are not intended to limit the technological features set forth herein to particular embodiments, and include various changes, equivalents, and/or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise.

As used herein, each of such phrases as "A or B" or "at least one of A and/or B" may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly or via another element (e.g., a third element).

The term "configured (or set) to . . . " used in the disclosure may be interchangeably used with the terms "suitable for . . . ," "having the capacity to . . . ," "adapted to . . . ," "made to . . . ," "capable of . . . ," or "designed to . . . " in a hardware or software level depending on the situation. In a certain situation, the term "a device configured to . . . " may refer to "the device being capable of . . . " with another device or parts. For example, "a processor configured (set) to perform A, B, and C" may refer, for example, and without limitation, to a dedicated processor (for example, an embedded processor) for performing a corresponding operation, or a generic-purpose processor (for example, a central processing unit (CPU) or an application processor (AP)), or the like, for performing corresponding operations by executing one or more software programs stored in a memory device.

In the following description, a protocol refers to an image-capturing technique that is requested by a doctor, for obtaining a medical image of a patient or an examinee. For example, the image-capturing technique may refer to a measurement part and an image-capturing direction of an object, or a measurement part and an image-capturing operation (that is, a posture of an examinee during image capturing) of the object.

In the following description, first to fifth protocol lists refer to information of a plurality of protocols listed according to a predetermined order. For example, the first protocol list refers to a protocol list that is generated by a doctor or an electronic device used by the doctor, and the order of the protocols may be determined based on a detected user's (for example, doctor's) input or randomly. In another example, the second protocol list refers to rearrangement of the order of the protocols included in the first protocol list based on a predefined regulation (for example, a type of a detector or a radiographic image capturing position). In still another example, the third protocol list may refer to rearrangement of the order of the protocols included in the second protocol list based on a detected user's (for example, radiological technologist's) input. In yet another example, the fourth protocol list may be generated in a similar method to the first protocol list, and may include protocols regarding an examinee different from the examinee regarding the first protocol list, or may include protocols regarding a different measurement part of the same examinee. In further example, the fifth protocol list may refer to rearrangement of the order of the protocols included in the fourth protocol list based on refined user pattern information. The definitions of the first to fifth protocol lists are merely examples, and are not limited to a specific embodiment.

In the following description, a first group and a second group refer to protocol groups which are classified by a type of a detector (table or stand), as will be described below. For example, the first group may include protocols in which the type of the detector is a table, and the second group may include protocols in which the type of the detector is a stand. The definitions of the first group and the second group are merely examples, and are not limited to a specific embodiment.

In the following description, an object refers to a patient or an examinee which are examined by a radiography device. For convenience of explanation, the object and the examinee may be interchangeably used according to a situation.

FIG. 1 illustrates a network environment including a radiography system according to various embodiments.

Referring to FIG. 1, the network environment 100 includes another electronic device 110, a server 120, and a radiography system 130. Another electronic device 110 includes various types of electronic devices which diagnose and analyze a health condition of an object, and generate information related to the health condition. For example, another electronic device 110 may be a desk top personal computer (PC), a laptop PC, a net book computer, a smartphone, a tablet PC, a personal digital assistant (PDA), a portable multimedia player (PMP), or a wearable device. Another electronic device 110 generates information related to the object based on an input received from a user (for example, a doctor) of another electronic device 110. For example, the information related to the object may include a protocol list.

The server 120 collects and transmits various data which are generated from another electronic device 110 or the radiography system 130. In an embodiment, the server 120 may be a server which transmits and receives information to and from a plurality of medical devices in a hospital or through an external network (for example, picture archaizing and communication system (PACS)).

The radiography system 130 refers to an overall system that obtains a medical image regarding the object by using radiation. For example, the radiography system 130 may obtain the medical image by using computer tomography (CT) or X-RAY. The radiography system 130 includes an electronic device 132 and a radiography device 134.

The radiography device 134 refers to a device for capturing the medical image. The radiography device 134 may be a fixed device performing image capturing in a predefined region (for example, a laboratory), and a movable device which moves to a region where an examinee is located (for example, a patient room) and then performs image capturing. The electronic device 132 refers to electronic equipment which performs an overall function to control the image-capturing operation of the radiography device 134. For example, the electronic device 132 may be a work station.

When the radiography device 134 is the fixed device, the radiography device 134 may be installed in a predefined region (for example, a laboratory), and may not leave from the predefined region. However, the radiography device 134 may perform image capturing while moving within a predetermined range in the predefined region. When the radiography device 134 is the fixed device, the radiography system 130 may further include a table and a stand although they are not illustrated in FIG. 1. The table and the stand include a detector for detecting a beam (for example, X-ray) generated from the radiography device 134. The object may be examined on the table or the stand based on an image-capturing technique indicated by each protocol, and the user of the radiography system 130 may obtain a medical image regarding the object from the detector included in the table or the stand.

When the radiography device 134 is the movable device, the radiography device 134 may further include a moving wheel. In this case, the radiography device 134 may move to a place where the object is located by using the moving wheel, and then may perform image capturing by using an already received protocol list.

The radiography system 130 may communicate with another electronic device 110 or the server 120 through a network connected wiredly or wirelessly. In an embodiment, when another electronic device 110 generates a protocol list at step 145 as shown in FIG. 1, another electronic device 110 may transmit the protocol list to the radiography device 134 included in the radiography system 130 through the server 120 and the electronic device 132 at step 150. At step 155, the radiography device 134 performs image capturing with respect to the object based on the received protocol list. At step 160, the radiography device 134 may transmit the captured image to another electronic device 110 through the electronic device 132 and the server 120. At step 165, another electronic device (or the user of another electronic device 110) may analyze and diagnose the health condition of the object by using the received image.

Although FIG. 1 depicts only the operation of transmitting the generated protocol list to the radiography device 134 through the server 120 and the electronic device 132, the generated protocol list may be directly transmitted to the electronic device 132 from another electronic device 110, or may be directly transmitted to the radiography device 134 from another electronic device 110 according to various implementation methods.

Figure 2:
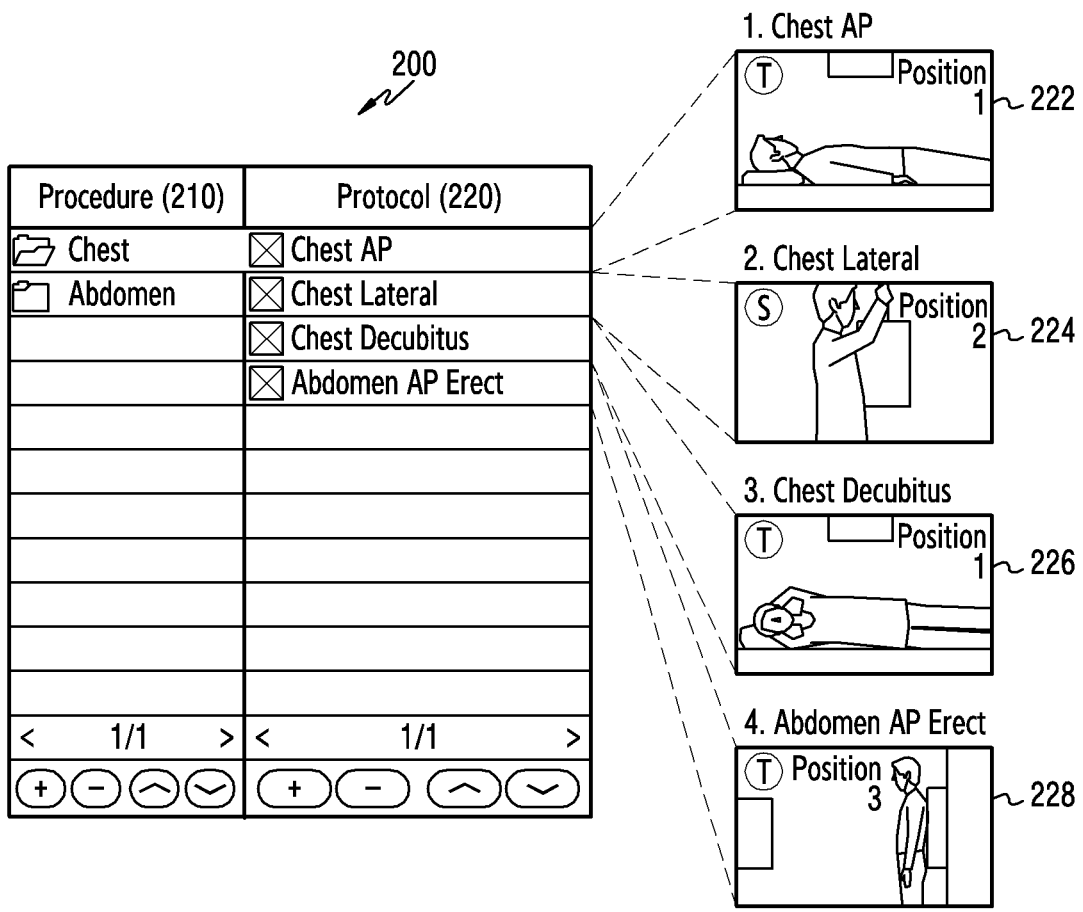
FIG. 2 is a view illustrating an example of a user interface (UI) indicating a list of protocols received from another electronic device.

FIG. 2 illustrates an example of a UI indicating the protocol list received from another electronic device.

The UI 200 is generated at another electronic device 110 and is transmitted to the electronic device 132 or the radiography device 134. Referring to FIG. 2, the UI 200 includes a procedure list 210 and a protocol list 220. Although FIG. 2 depicts that the UI 200 includes both the procedure list 210 and the protocol list 220, the UI 200 may include only the procedure list 210 or may include only the protocol list 220 according to an implementation method.

In the disclosure, the procedure refers to data including information regarding a plurality of protocols. In an embodiment, the procedure may include information regarding a measurement part of the object requested by the user of another electronic device 110. For example, the measurement part may refer to a chest, an abdomen, or the like.

In the disclosure, the protocol refers to an image capturing technique that the user of the radiography system 130 (for example, a radiological technologist) intends to use to capture an image by using the radiography device 134. For example, the image capturing technique may refer to a measurement part and an image-capturing direction of the object or a measurement part and an image-capturing operation (that is, an examinee's posture during image capturing) of the object.

In an embodiment, the protocol list 220 may include a chest AP protocol, a chest lateral protocol, a chest decubitus protocol, and an abdomen AP erect protocol as shown in FIG. 2. The chest AP protocol indicates that the measurement part of the examinee is a chest and the image-capturing direction is an antero-posterior (AP) direction. In this case, the examinee is examined lying on the table T included in the radiography system 130, and the radiography device 134 is moved to a predefined position (position 1) and then performs image capturing as shown in example view 222. The chest lateral protocol indicates that the measurement part of the examinee is a chest, and the image-capturing operation is a lateral posture. In this case, as shown in example view 224, the examinee is examined standing by the stand S included in the radiography system 130, and the radiography device 134 is moved to a predefined position (position 2) and then performs image capturing with respect to the chest side surface of the examinee. The chest decubitus protocol indicates that the measurement part of the examinee is a chest and the image-capturing operation is a posture in which the examinee lies on his/her side (decubitus). In this case, as shown in example view 226, the examinee is examined lying on the table, and the radiography device is moved to position 1, and then performs image capturing. The abdomen AP erect protocol indicates that the measurement part of the examinee is an abdomen, and the image-capturing direction is the AP direction, and the image-capturing operation of the examinee is a posture in which the examinee stands upright (erect). In this case, as shown in example view 228, the examinee is examined standing in front of the stand, and the radiography device 134 is moved to a predefined position (position 3) and then performs image capturing. In the disclosure, the respective numbers indicating the positions are merely indexes indicating specific position information (for example, coordinate values indicating positions), and do not directly indicate specific position information.

As described above with reference to FIG. 2, based on the plurality of protocols included in the procedure list or the protocol list, received by the radiography system 130 from another electronic device 110 through the server 120, a measurement part of the object, an image-capturing position of the radiography device, and an image-capturing operation of the object are determined. When image capturing is performed, the user of the radiography system 130 considers an image-capturing order to minimize a moving path of the radiography device and a motion path of the object. However, since the order of the protocols included in the received protocol list may not be consistent with the image-capturing order that is considered by the user of the radiography system 130, the user should rearrange the order of the protocols.

Accordingly, various embodiments of the disclosure described below provide an apparatus for automatically rearranging the order of the received protocols based on a using pattern of the user and a predefined classification criterion, and an operation method thereof.

Figure 3:
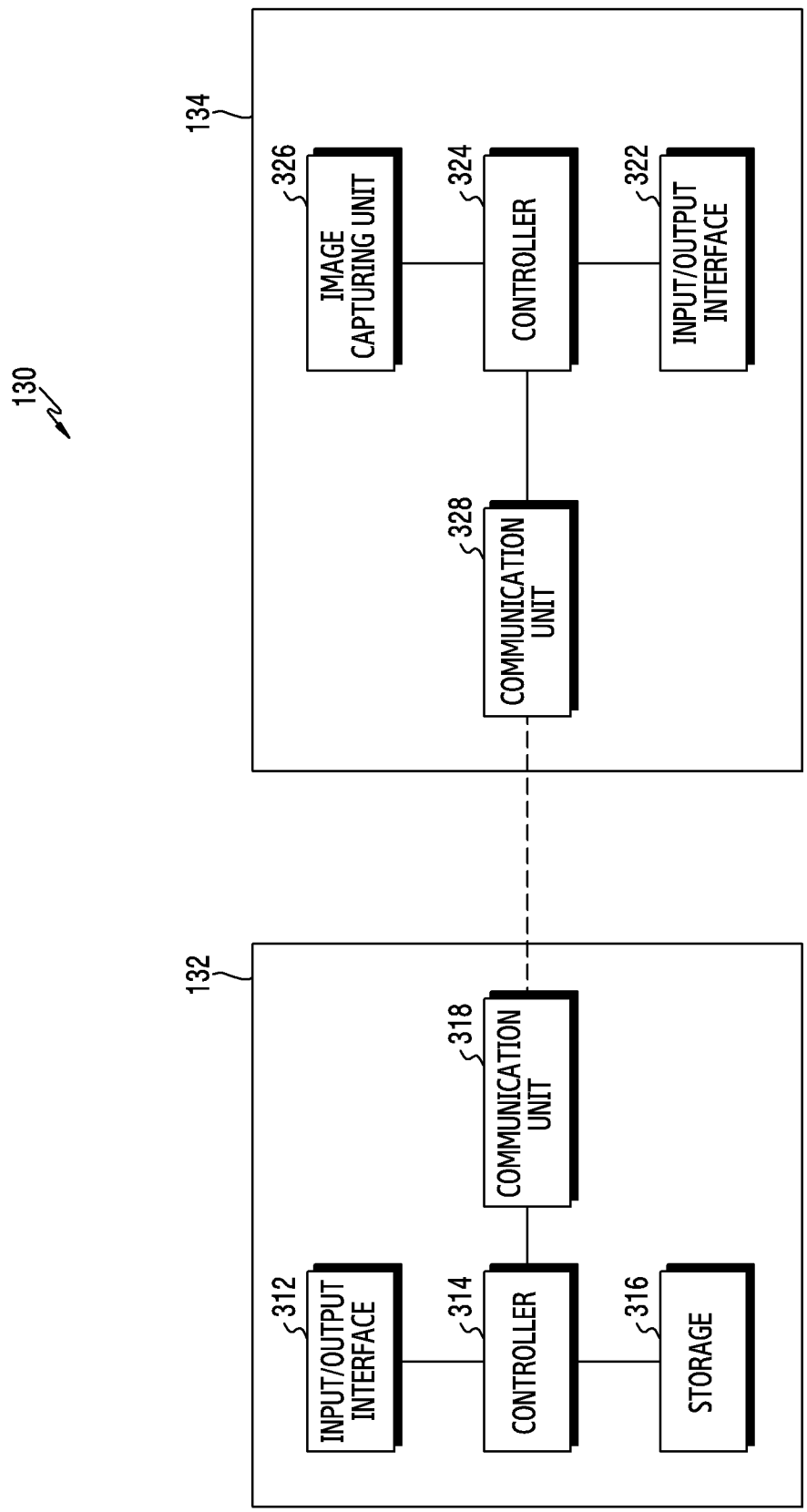
FIG. 3 is a block diagram illustrating a functional configuration of a radiography system according to various embodiments.

FIG. 3 is a block diagram illustrating a functional configuration of the radiography system according to various embodiments. The term " . . . unit" and the terms ending with the suffix "-er" or "-or" used herein refer to a unit processing at least one function or operation, and these terms may refer to hardware, software, or a combination of hardware and software.

The electronic device 132 includes an input/output interface 312, a controller 314, a storage 316, and a communication unit 318.

The input/output interface 312 provides an interface for the user to control the electronic device 132. For example, the input/output interface 312 may be a controller, a keyboard, a mouse, a touch pad, a monitor, and a touch screen. The input/output interface 312 may detect an input received from the user, and may transmit information regarding the detected input to the controller 314. In addition, the input/output interface 312 may receive various data from the controller, and may output the received data to the user.

The storage 316 may store a control command code for controlling the electronic device 132, control data, or user data. For example, the storage 316 may include an application, an operating system (OS), middleware, and a device driver. The storage 316 may include one or more of a volatile memory or a non-volatile memory. The volatile memory may include a dynamic random access memory (DRAM), a static RAM (SRAM), a synchronous DRAM (SDRAM), a phase-change RANI (PRAM), a magnetic RAM (MRAM), a resistive RANI (RRAM), a ferroelectric RAM (FeRAM), or the like. The non-volatile memory may include a read only memory (ROM), a programmable ROM (PROM), an electrically programmable ROM (EPROM), an electrically erasable ROM (EEPROM), a flash memory, or the like. The storage 316 may include a non-volatile memory such as a hard disk drive (HDD), a solid state disk (SSD), an embedded multi media card (eMMC), or a universal flash storage (UFS).

The communication unit 318 performs an overall operation for the electronic device 132 to communicate with the radiography device 134 through a wired or wireless network. In an embodiment, the communication unit 318 may be configured for the electronic device 132 to communicate with the radiography device 134 by using a transmission control protocol (TCP). In another embodiment, when the electronic device 132 communicates with the radiography device 134 through a wireless network, the communication unit 318 may perform an operation for processing transmitted and received signals in a baseband, or for generating as a radio frequency (RF) signal. The wireless network may use short-range communication technology such as Bluetooth, Bluetooth low energy (BLE), WiFi Direct, device-to-device (D2D) of long term evolution (LTE), or the like, and may use long-range communication technology such as LTE, world wide interoperability for microwave access (WiMAX), or the like.

Although FIG. 3 depicts that the communication unit 318 performs the operation for the electronic device 132 to communicate with the radiography device 134, the communication unit 318 may perform an overall operation for communicating with another electronic device 110 or the server 120. For example, the communication unit 318 may exchange data with another electronic device 110, the server 120, and the radiography device 134 by using at least one transceiver.

The controller 314 may include at least one processor or micro processor for controlling overall operations of the electronic device 132, or may be a part of the processor. In addition, the controller 314 may include an application processor (AP) for controlling an upper layer such as an application program or the like, and a communication processor (CP) for controlling communication.

The controller 314 may be functionally coupled to other elements to control the overall operations of the electronic device 132. In an embodiment, the controller 314 may control the communication unit 318 to receive a protocol list from the server 120 or another electronic device 110, and may rearrange the order of a plurality of protocols included in the protocol list, based on an algorithm stored in the storage 316 or user pattern information. In addition, the controller 314 may control the communication unit 318 to transmit a protocol list including the protocols of the rearranged order to the radiography device 134. In addition, the controller 314 may refine the user pattern information, based on the order of the protocols rearranged based on a user input. The controller 314 may store the refined user pattern information in the storage 316.

The radiography device 134 includes an input/output interface 322, a controller 324, an image capturing unit 326, and a communication unit 328.

The input/output interface 322 provides an interface for the user to control the radiography device 134. For example, the input/output interface 322 may be a controller, a keyboard, a mouse, a touch pad, a monitor, and a touch screen. In an embodiment, the input/output interface 322 may detect an input received from the user, and may transmit information regarding the detected input to the controller 324. In another embodiment, the input/output interface 322 may be configured to display a UI including a protocol list for the user.

The communication unit 328 performs an overall operation for the radiography device 134 to communicate with the electronic device 132 through a wired or wireless network. In an embodiment, the communication unit 328 may be configured for the radiography device 134 to communicate with the electronic device 132 by using a TCP. In another embodiment, when the radiography device 134 communicates with the electronic device 132 through a wireless network, the communication unit 328 may perform an operation for processing transmitted and received signals in a baseband, or for generating as an RF signal. The wireless network may use short-range communication technology such as Bluetooth, BLE, WiFi Direct, D2D of LTE, or the like, and may use long-range communication technology such as LTE, WiMAX, or the like.

Although FIG. 3 depicts that the communication unit 328 performs the operation for the radiography device 134 to communicate with the electronic device 132, the communication unit 328 may perform an overall operation for communicating with another electronic device 110 or the server 120. For example, the communication unit 328 may exchange data with another electronic device 110, the server 120, and the electronic device 132 by using at least one transceiver.

The image capturing unit 326 performs an overall function for capturing an image by using radiation. For example, the image capturing unit 326 may emit X-rays having a short wavelength by using a high voltage. In this case, the detector (not shown) of the table or stand type included in the radiography system 130 may detect the emitted X-rays, and may grasp the internal structure of the object.

The controller 324 may include at least one processor or micro processor for controlling the overall operations of the radiography device 134, or may be a part of the processor. In addition, the controller 324 may include an AP for controlling an upper layer such as an application program or the like, and a CP for controlling communication.

The controller 324 may be functionally coupled to other elements to control the overall operations of the radiography device 134. In an embodiment, the controller 324 may control the communication unit 328 to receive the rearranged protocol list from the electronic device 132. In another embodiment, the controller 324 may control the image capturing unit 326 to perform image capturing based on the received protocol list. When image capturing with respect to one of the plurality of protocols is completed, the controller 324 may generate a UI indicating that the imaging capturing with respect to the protocol is completed. The controller 324 may control the input/output interface 322 to output the generated UI for the user.

As described above, the electronic device in the radiography system may include a transceiver, and at least one processor functionally coupled to the transceiver. The at least one processor may be configured to: control to receive, from the server, information regarding a first protocol list including a plurality of protocols; identify position information of the radiography device which performs image capturing with respect to each of the plurality of protocols, and a type of a detector which detects a beam generated from the radiography device; generate a second protocol list by rearranging the order of the plurality of protocols, based on at least one of the position information of the radiography device and the type of the detector; and control to transmit information regarding the second protocol list to the radiography device. The image capturing position information of the radiography device, and the type of the detector may be determined based on an image capturing technique indicated by each of the plurality of protocols.

In addition, the at least one processor may further be configured to: classify the plurality of protocols into a first group and a second group, based on the type of the detector; rearrange an order of at least one protocol included in each of the first group and the second group, based on the position information of the radiography device; and rearrange the order of the at least one protocol rearranged in each of the first group and the second group, based on user pattern information. The user pattern information may correspond to each of a plurality of user accounts for accessing the electronic device, and may be determined based on at least one of the position information of the radiography device, the image capturing part information of the object, and the image capturing operation information of the object.

In addition, the at least one processor may further be configured to: detect an access to the electronic device by using at least one user account of the plurality of user accounts; control to receive information regarding a detected user input from the radiography device; based on the information regarding the user input, generate a third protocol list by rearranging the order of the plurality of protocols included in the second protocol list; based on the generated third protocol list, refine the user pattern information corresponding to the user account; and store the refined user pattern information.

In addition, the at least one processor may further be configured to: control to receive a fourth protocol list including a plurality of other protocols from the server, detect an access to the electronic device by using the user account, generate a fifth protocol list by rearranging the plurality of other protocols based on the refined user pattern information, and control to transmit information regarding the fifth protocol list to the radiography device.

In addition, the at least one processor may further be configured to: control to receive, from the radiography device, a message indicating that image capturing with respect to one of the plurality of protocols included in the second protocol list is completed; and control to transmit, to the radiography device, position information of the radiography device corresponding to a next protocol.

In addition, the at least one processor may further be configured to control to transmit, to the radiography device, UI information in which the protocol for which the image capturing is completed is marked differently from the other protocols of the plurality of protocols.

As described above, the radiography device in the radiography system may include: a transceiver; and at least one processor functionally coupled to the transceiver. The at least one processor may be configured to: control to receive information regarding a second protocol list from an electronic device; and, based on an order of a plurality of protocols included in the second protocol list, perform image capturing with respect to each of the plurality of protocols. The second protocol list may be generated by rearranging, by the electronic device, an order of the plurality of protocols included in a first protocol list, and may be generated based on at least one of position information of the radiography device regarding each of the plurality of protocols, and a type of a detector for detecting a beam generated from the radiography device. The image capturing position information of the radiography device, and the type of the detector may be determined based on an image capturing technique indicated by each of the plurality of protocols.

In addition, the second protocol list may be generated based on user pattern information stored in the electronic device, in addition to the position information and the type of the detector, and the user pattern information may correspond to each of a plurality of user accounts for accessing the electronic device, and may be determined based on at least one of position information of the radiography device, image capturing part information of the object, and image capturing operation information of the object.

In addition, the user pattern information may be refined by the electronic device, based on information regarding a user input detected from the electronic device.

In addition, the at least one processor may further be configured to: when image capturing with respect to one of the plurality of protocols is completed, display a UI indicating that the image capturing with respect to the protocol is completed; move to an image capturing position regarding a protocol which is the next to the protocol from among the plurality of protocols included in the second protocol list; and perform image capturing with respect to the protocol corresponding to the next order at the moved image capturing position.

In addition, the at least one processor may further be configured to, when the image capturing with respect to one of the plurality of protocols is completed, display a UI in which the protocol for which the image capturing is completed is marked differently from the other protocols.

Figure 4:
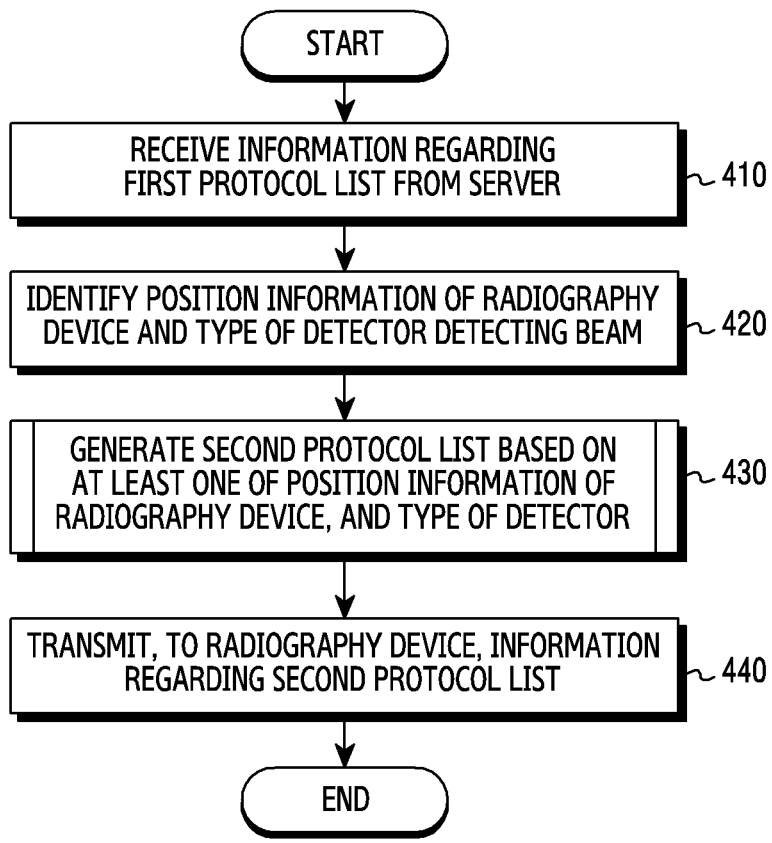
FIG. 4 is a flowchart illustrating an operation of an electronic device for rearranging an order of a plurality of protocols according to various embodiments.

FIG. 4 illustrates a flowchart of operations of the electronic device 132 for rearranging an order of a plurality of protocols according to various embodiments. More specifically, FIG. 4 illustrates a flow of operations of processing by the controller 314. However, the operations illustrated in FIG. 4 may be performed by the processor included in another electronic device 110 or the server 120 or the controller 324 included in the radiography system according to various implementation methods.

Referring to FIG. 4, at step 410, the controller 314 controls the communication unit 318 to receive information regarding a first protocol list from another electronic device 110 or the server 120. The information regarding the first protocol list may include a protocol list or a procedure list generated at another electronic device 110. An arrangement order of the plurality of protocols included in the first protocol list may be determined by another electronic device 110 or the user of another electronic device 110, or randomly.

At step 420, the controller 314 may identify image-capturing position information and a type of the detector which correspond to each of the plurality of protocols included in the received first protocol list. The image-capturing position information includes information of a position (for example, three-dimensional coordinate values) to which the radiography device 134 should move to perform image capturing according to an image-capturing technique indicated by the protocol. The type of the detector refers to a type of the detector that detects a beam generated from the image capturing unit 326. The type of the detector includes a table type and a stand type. In other words, the controller 314 may identify a position of the radiography device 134 that is required to perform image capturing, and may identify on which of the table or stand the object will be examined, with respect to each of the received protocols, by identifying the image-capturing position information and the type of the detector.

At step 430, the controller 314 generates a second protocol list by rearranging the order of the protocols, based on the identified image-capturing position information and the type of the detector. An order of the protocols included in the second protocol list may be rearranged to minimize a moving path of the radiography device 134 or a motion path of the object.

At step 440, the controller 314 controls the communication unit 318 to transmit information regarding the generated second protocol list to the radiography device 134. When the operations of steps 410 to 430 are directly performed by the controller 324 included in the radiography device 134, the controller 324 may not perform the operation of step 440.

Figure 5:
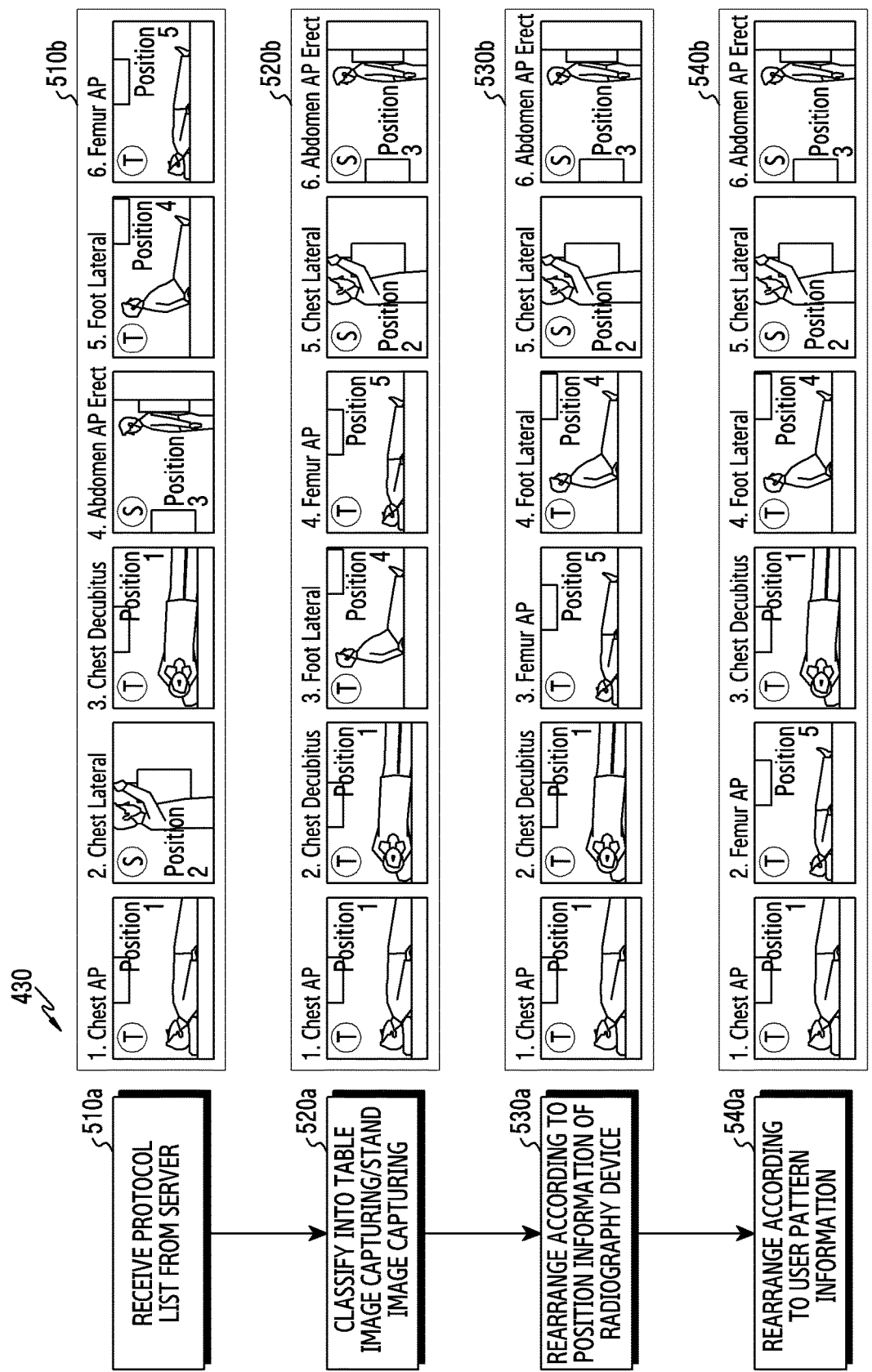
FIG. 5 is a view illustrating an example of an operation of rearranging an order of a plurality of protocols according to an embodiment.

FIG. 5 illustrates an example of the operation of rearranging the order of the plurality of protocols according to an embodiment. Respective operations illustrated in FIG. 5 are detailed operations of step 430 of FIG. 4. Embodiments described hereinafter are merely examples, and the order of the steps or the order of the protocols is not limited to examples illustrated in FIG. 5. In addition, all of operations 510a to 540a are not necessarily implemented, and at least one operation may be omitted.

The order of the protocols received by the controller 314 from the server 120 or another electronic device 120 at step 510a corresponds to example view 510b. In the disclosure, the respective numbers indicating the positions are merely indexes indicating specific position information (for example, coordinate values indicating positions), and do not directly indicate specific position information. According to the order of the protocols illustrated in example view 510b, the user of the radiography system 130 should perform image capturing in order of chest AP, chest lateral, chest decubitus, chest AP erect, foot lateral, and femur AP. When the user follows the order, the object should move in order of table, stand, table, stand, table, and table, and the radiography device 134 should move in order of position 1 (that is, a center above the table), position 2 (that is, a center at a side of the stand), position 1, position 3 (that is, a lower portion of the front of the stand), position 4 (that is, a right end portion above the table), and position 5 (that is, a right center portion above the table). In other words, the radiography device 134 should move to position 1 to perform image capturing with respect to the chest AP protocol, should move to position 2 to perform image capturing with respect to the chest lateral protocol, and then should return to position 1 to perform image capturing with respect to the chest decubitus protocol.

At step 520a, the controller 314 classifies the protocols based on the type of the detector of each of the protocols (that is, the table type or stand type). When the operation of step 520a is performed, the protocols are rearranged in the order illustrated in example view 520b. In this case, the object may be positioned on the table during the examination for the chest AP, chest decubitus, foot lateral, and femur AP, and may be positioned on the stand during the examination for the chest lateral and the abdomen AP erect. In addition, according to the order illustrated in example view 520b, the radiography device 134 should move in order of position 1, position 1, position 4, position 5, position 2, and position 3.

At step 530a, the controller 314 rearranges the order of the protocols based on image-capturing position information. When the operation of step 530a is performed, the protocols are rearranged in order illustrated in example view 530b. In this case, the type of the detector on which the object is positioned is the same as in the previous example, and the radiography device 134 should move in order of position 1, position 1, position 5, position 4, position 2, and position 3.

At step 540a, the controller 314 rearranges the order of the protocols, based on user pattern information pre-stored in the storage 316 or a detected user input. The user pattern information refers to information that is generated by analyzing a using pattern of a specific user using the radiography system 130.

In an embodiment regarding the operation of step 540a, a motion path of the object may be considered first. For example, when the user pattern information of the specific user is set to consider the motion path of the object first, the protocols may be rearranged in order illustrated in example view 540b. In another example, the user may directly rearrange the order of the protocols to minimize the motion path of the object. In this case, the object is not required to move separately during the examination for the chest AP and the femur AP, whereas the radiography device 134 should move in order of position 1 and position 5.

In another embodiment regarding the operation of step 540a, the moving path of the radiography device 134 may be considered first. For example, when the user pattern information of the specific user is set to consider the moving path of the radiography device 134 first, the protocols may be rearranged in order illustrated in example view 530b. In this case, the object should continuously change the posture during the examination for the chest AP, chest decubitus, and femur AP, whereas the radiography device 134 is not required to move separately while performing image capturing for the chest AP and the chest decubitus.

Figure 6A:
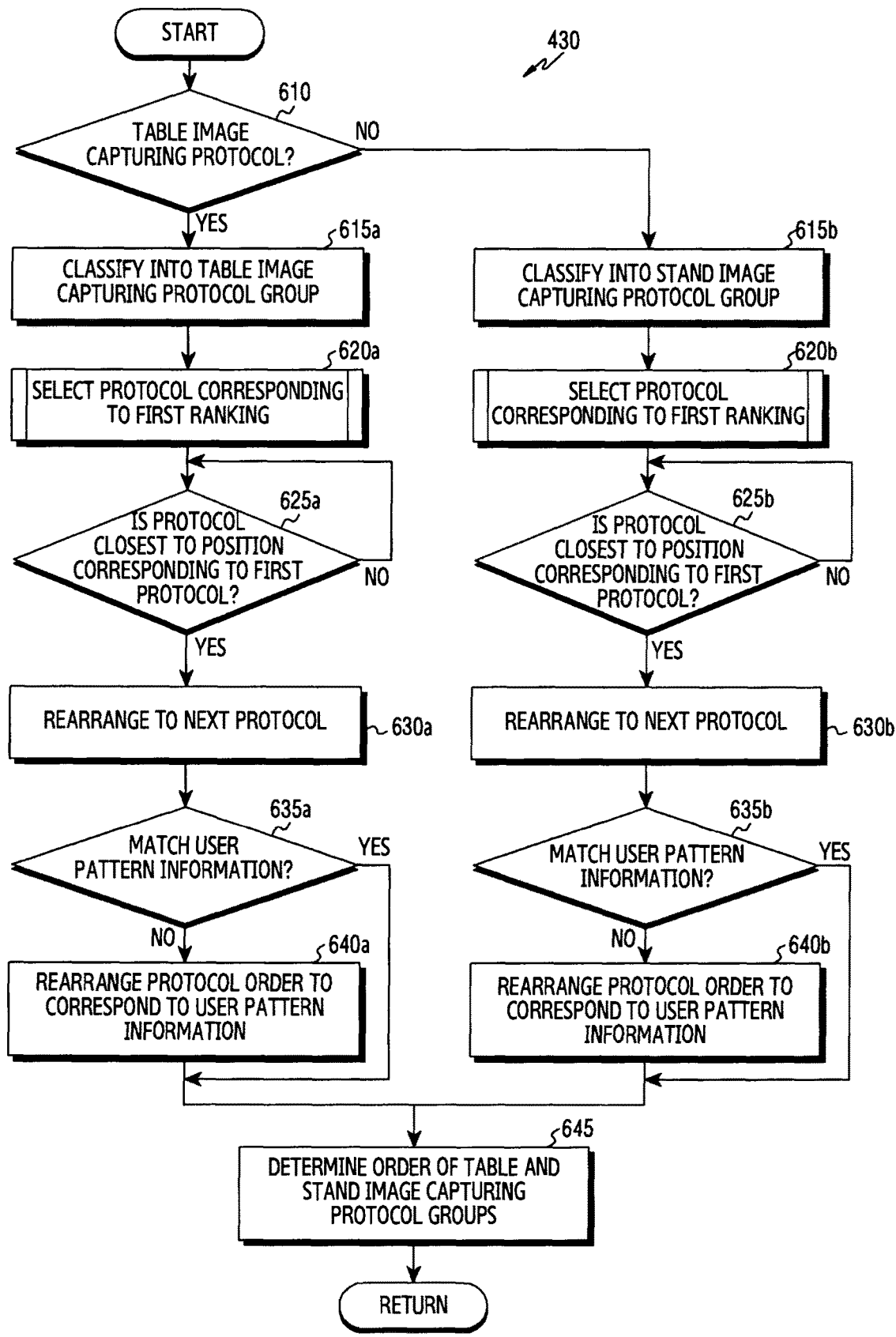
FIGS. 6A and 6B are flowcharts of a specific operation of an electronic device for rearranging an order of a plurality of protocols according to various embodiments.
Figure 6B:
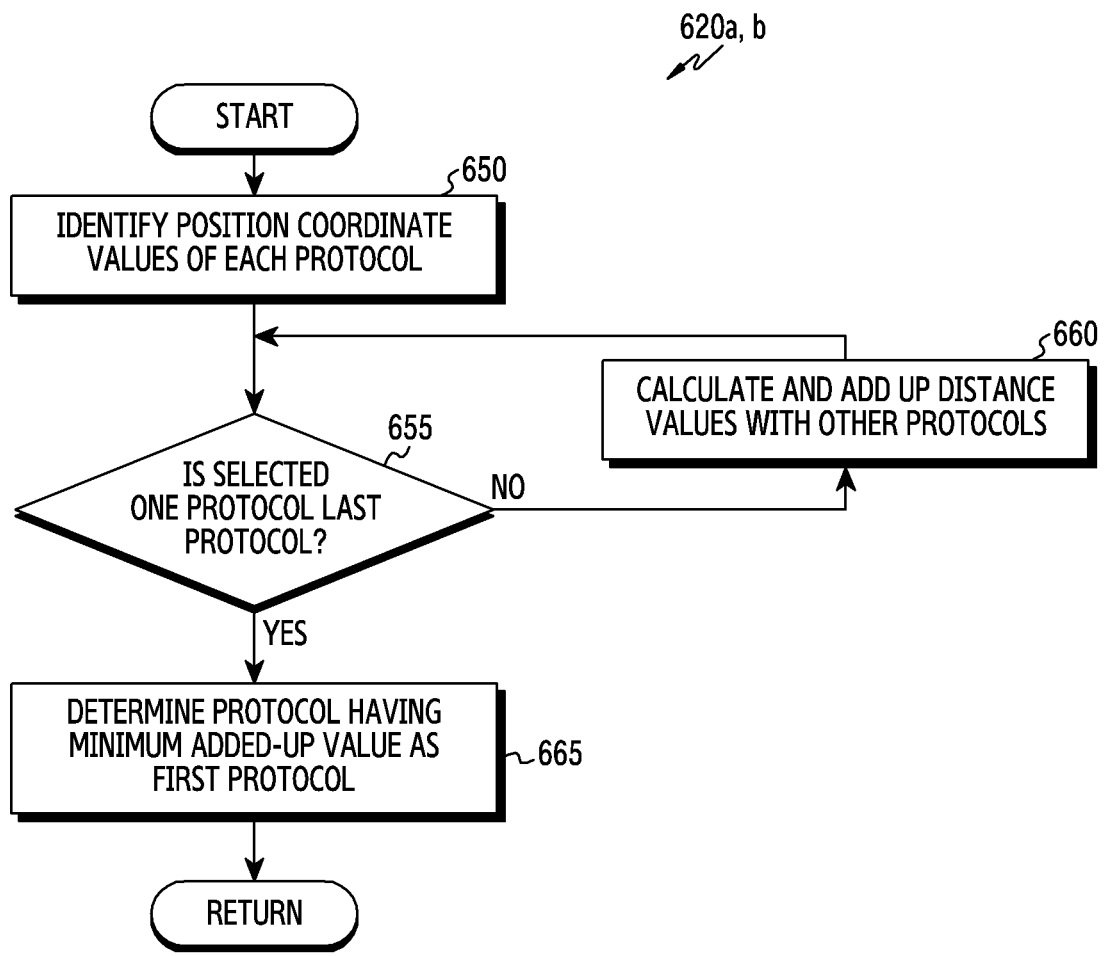

FIGS. 6A and 6B illustrate specific operation flowcharts of the electronic device 132 for rearranging the order of a plurality of protocols according to various embodiments. FIG. 6A illustrates the operation of step 430 of FIG. 4 in more detail, and FIG. 6B illustrates operations of step 620a or 620b of FIG. 6A in more detail.

Referring to FIG. 6A, at step 610, the controller 314 may determine whether the type of the detector of the plurality of protocols included in the received first protocol list is the table type or not. When the detector type is the table type, the controller 314 classifies the corresponding protocols into a table group at step 615a. In addition, when the detector type is not the table type, the controller 314 classifies the corresponding protocols into a stand group at step 615b.

At step 620a, the controller 314 selects a protocol corresponding to the first ranking. In an embodiment, the controller 314 may determine a protocol positioned at the top in the protocol list received from another electronic device 110, as the protocol corresponding to the first ranking. In another embodiment, as shown in FIG. 6B, the controller 314 may select the protocol corresponding to the first ranking, based on a distance between the protocols.

Referring to FIG. 6B, at step 650, the controller 314 identifies position coordinate values of the received protocols. For example, the position coordinate values may be three-dimensional coordinate values (x, y, z).

At step 655, the controller 314 may determine whether the selected one protocol is the last protocol. When the selected one protocol is not the last protocol, the controller 314 may calculate distance values between the selected one protocol and the other protocols, and may add up the calculated distance values at step 660. For example, referring to example view 520b of FIG. 5, it is assumed that the controller 314 selects the chest AP protocol. When the selected chest AP protocol is not the last protocol, the controller 314 calculates distance values between the position corresponding to the chest AP protocol, and positions corresponding to the other protocols, and may add up the calculated distance values. Thereafter, the controller 314 may select the chest decubitus protocol. When the selected chest decubitus protocol is not the last protocol, the controller 314 may calculate distance values between the position corresponding to the chest decubitus protocol, and positions corresponding to the other protocols, and may add up the calculated distance values. In the same way, the controller 314 may calculate distance values between the positions corresponding to the foot lateral, femur AP, and chest lateral protocols, and positions corresponding to the other protocols, and may add up the calculated distance values.

When the protocol selected by the controller 314 is the last protocol (for example, when the abdomen AP erect protocol is selected in example view 520b of FIG. 5), the controller 314 performs an operation of step 665. More specifically, the controller 314 compares the added-up values calculated at step 660 and may determine a protocol that has the minimum added-up value as the first protocol.

When the protocol of the first ranking is selected at step 620a, the controller 314 may determine whether position information corresponding to a protocol selected from the other protocols is the closest to position information corresponding to the selected protocol of the first ranking at step 625a. For example, referring to example view 520b of FIG. 5, it is assumed that the protocol selected as the first ranking through step 620a is chest AP (position 1). The controller 314 may calculate a position coordinate value and a distance corresponding to the chest AP protocol, by using position coordinate values of the chest decubitus protocol (position 1), the foot lateral protocol (position 4), and the femur AP protocol (position 5). In this case, since the image-capturing position regarding the chest decubitus protocol is the same as (that is, the closest to) the image-capturing position regarding the chest AP protocol, the controller 314 rearranges the chest decubitus protocol to be the next protocol to the first selected chest AP protocol at step 630a. In the above-described way, the controller 314 may rearrange the femur AP protocol which is the closest to the image-capturing position of the chest decubitus protocol to be the next protocol.

At step 635a, the controller 314 may determine whether the order of the rearranged protocols is consistent with user pattern information. When the order of the rearranged protocols is not consistent with the user pattern information, the controller 314 may rearrange the order of the protocols to correspond to the user pattern information at step 640a. For example, when user pattern information for a specific user is set to consider a motion path of the object first, the femur AP protocol is rearranged to be the next protocol to the chest AP protocol as shown in example view 540b of FIG. 5. When the order of the rearranged protocols is consistent with the user pattern information, the controller 314 does not additionally rearrange the order of the protocols.

The controller 314 performs operations of steps 620b to 640b with respect to the protocols classified into the stand image-capturing protocol group. More specifically, the controller 314 selects a protocol of the first ranking from the stand image-capturing protocol group at step 620b, and determines a protocol which is the closest to the position corresponding to the protocol selected as the first ranking at steps 625b and 630b. Thereafter, the controller 314 rearranges the rearranged protocols to correspond to user pattern information at steps 635b and 640b.

At step 645, the controller 314 generates the second protocol list by determining a group from the rearranged table image-capturing protocol group and the rearranged stand image-capturing protocol group that is to be image-captured first.

As described above, the radiography system 130 may rearrange the order of the protocols based on a predefined algorithm or a pre-stored user pattern information. Hereinafter, a process of setting the user pattern information according to a specific user and refining through feedback will be described.

Figure 7A:
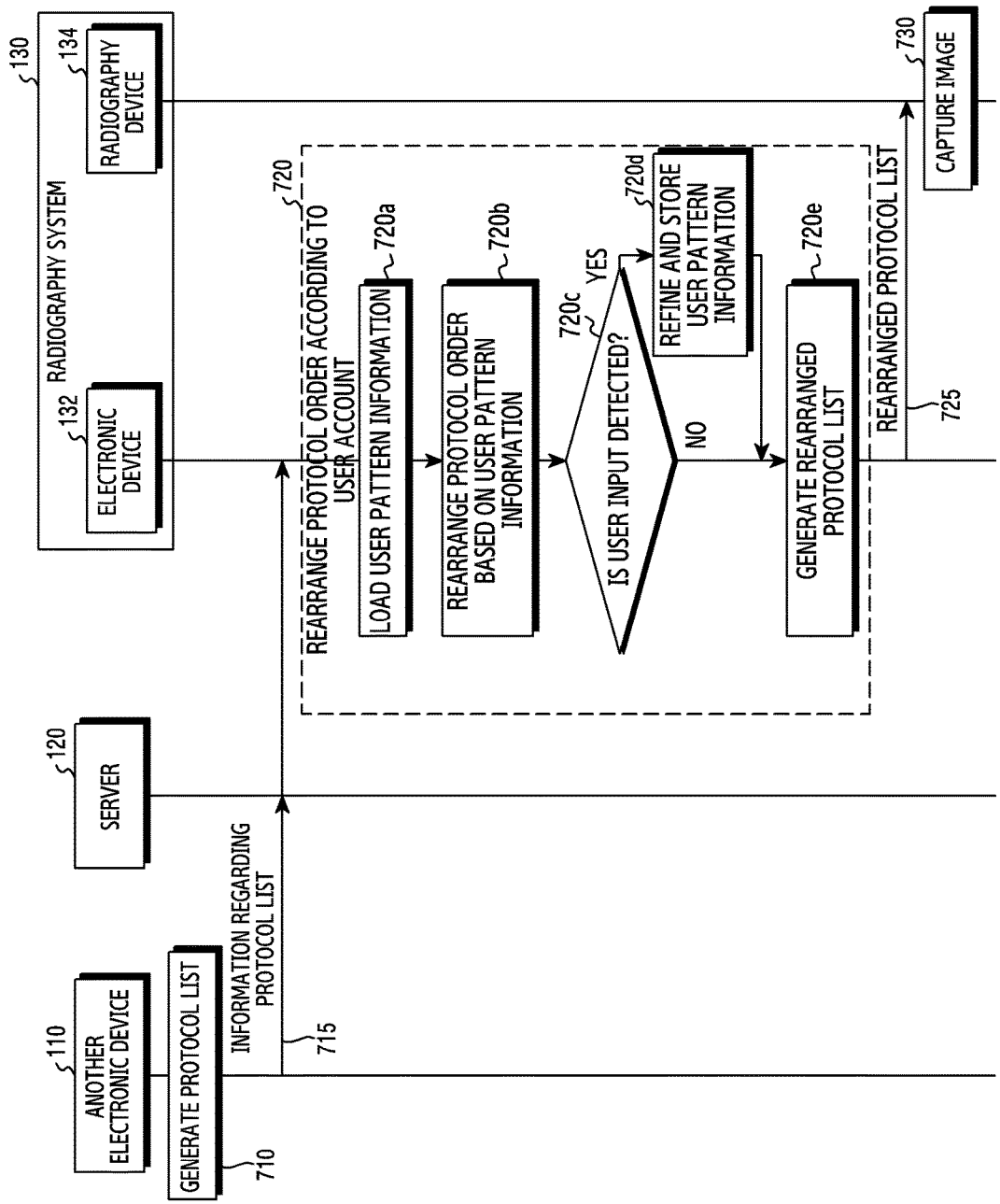
FIGS. 7A and 7B are views illustrating an example of an operation of setting user pattern information for each user.
Figure 7B:
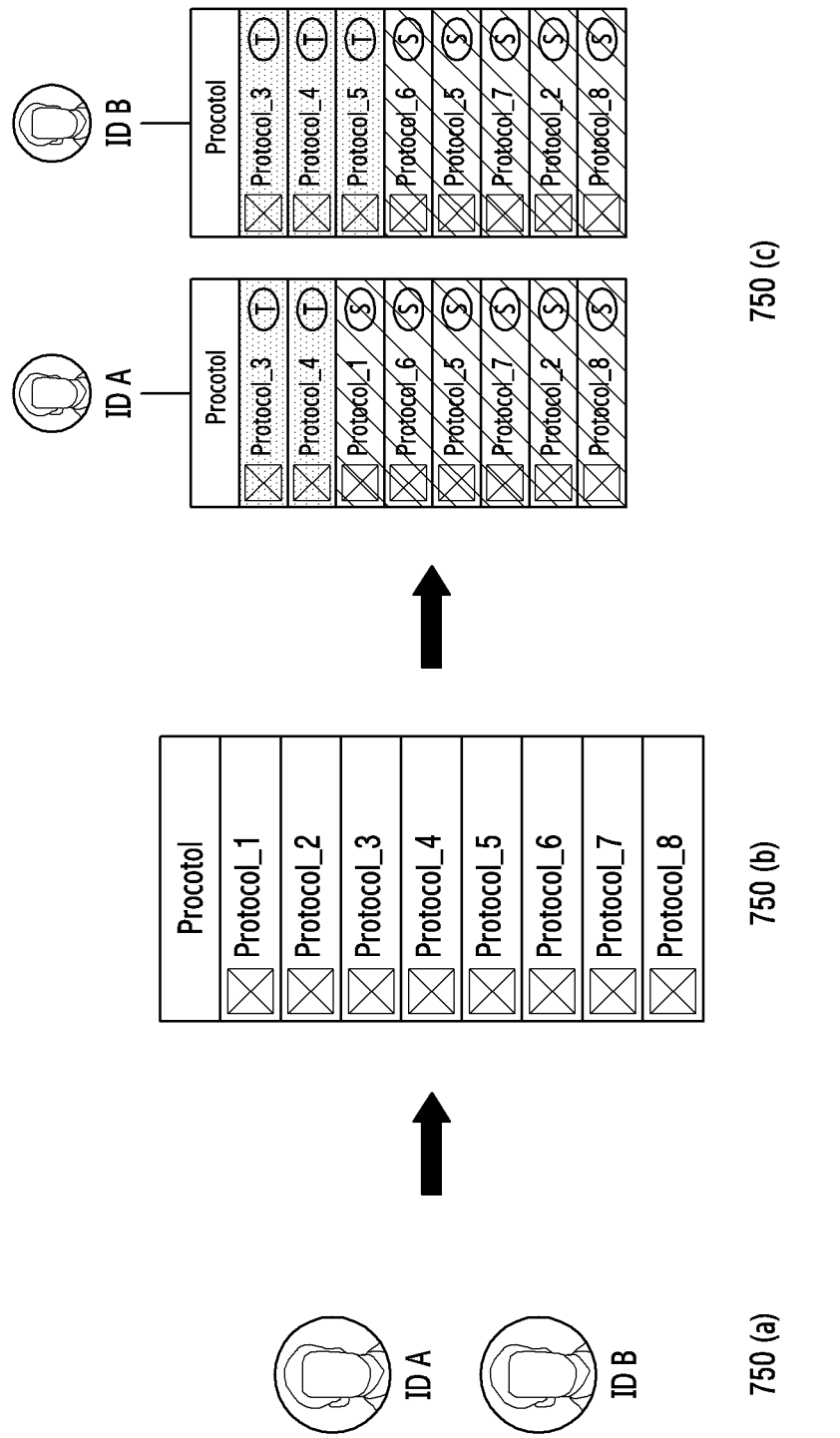

FIGS. 7A and 7B illustrate an example of an operation of setting user pattern information for each user according to various embodiments. FIG. 7A illustrates a signal flowchart for setting user pattern information for each user according to various embodiments, and FIG. 7B illustrates a UI displaying user pattern information set for each user for the user.

FIG. 7A illustrates that operations of steps 710 to 745 are performed by entities included in a network environment (for example, another electronic device 110, the server 120, the electronic device 132, and the radiography device 134), these operations are not limited to being performed by the entities, and each of the operations may be implemented by elements (for example, at least one processor) included in each of the entities.

Referring to FIG. 7A, another electronic device 100 generates a protocol list at step 710, and transmits the generated protocol list to the electronic device 132 through the server 120 at step 715.

At step 720, the electronic device 132 rearranges the order of the protocols according to a user account. The order of the protocols may be rearranged differently according to the user account.

At step 720a, the electronic device 132 loads user pattern information corresponding to a user account logged in (or accessing) the electronic device 132. The user pattern information may vary according to the user account. In addition, each user account may include at least one piece of user pattern information. When there is no user pattern information pre-stored regarding a specific user account, the electronic device 132 may not perform the operation of step 720a and may directly rearrange the order of the protocols at step 720b.

At step 720b, the electronic device 132 rearranges the order of the received protocols based on the loaded user pattern information. In an embodiment, when there is no user pattern information pre-stored, the electronic device 132 may rearrange the order of the protocols according to the operations of steps 520a and 530a. However, the order of steps 520a and 530a is not limited to that illustrated in FIG. 5, and step 520a may precede step 530a. In addition, one of steps 520a and step 530b may be omitted. In another embodiment, when there is user pattern information pre-stored, the electronic device 132 may rearrange the order of the protocols according to the stored user pattern information. For example, when the user pattern information of the specific user is set to consider classifying by the type of the detector as a first priority, and to consider the position of the radiography device as a second priority, the electronic device 132 may classify the order of the protocols based on the type of the detector first, and then may rearrange the order of the protocols based on the position of the radiography device. In another example, when the user pattern information of the specific user is set to consider classifying by the image-capturing operation of the object as a first priority, and to consider the type of the detector as a second priority, the electronic device 132 may classify the order of the protocols based on the image-capturing operation of the object, and then may rearrange the order of the protocols based on the type of the detector.

At step 720c, the electronic device 132 may determine whether an additional user input is detected. When the user input is detected, the electronic device 132 may rearrange the order of the protocols in response to the user input, and may refine the user pattern information in consideration of the detected user input at step 720d.

The user pattern information may be refined according to various implementation methods. In an embodiment, the user pattern information may be refined by calculating a statistical value of a pattern preferred by the user, based on data stored until a present time and the user input detected at step 720c. For example, the user pattern information of the specific user may be set to indicate that the first criterion is the type of the detector. In this case, when there are a large number of user inputs of selecting the type of the detector as the first priority, the user pattern information may be set to consider the type of the detector as the first priority although the user input is detected to consider the image-capturing operation of the object as the first priority at step 720c. On the other hand, when the user input is detected to consider the position of the radiography device as the first priority at step 720c, and the number of user inputs of selecting the position of the radiography device as the first priority is larger than the number of user inputs of selecting the type of the detector as the first priority, the electronic device 132 may refine the user pattern information of the user to consider the position of the radiography device as the first priority.

In another embodiment, when the type of the detector regarding a specific protocol is set to the table type, but is changed to the stand type based on the detected user input, the electronic device 132 may change the user pattern information, such that the type of the detector regarding the protocol corresponds to the stand type.

When the separate user input is not detected (that is, when the image capturing order considered by the user is consistent with the user pattern information) at step 725c, the electronic device 132 may not perform the operation of step 720d and may directly perform an operation of step 720e.

At step 720e, the electronic device 132 generates a protocol list rearranged based on the user pattern information and the user input. At step 725, the electronic device 132 may transmit information regarding the rearranged protocol list to the radiography device 134, and at step 730, the radiography device 134 performs image capturing based on the received protocol order.

The operations of steps 710 to 730 illustrated in FIG. 7A may be repeatedly performed every time another electronic device 110 generates other protocol lists. In this case, the electronic device 132 may rearrange the other protocol lists by using the user pattern information refined by the previous step, step 720.

As described above, the electronic device 132 may repeatedly refine the user pattern information through machine learning. The user of the electronic device 132 is not required to directly rearrange the received protocol list, by using the refined user pattern information. The user pattern information may be set differently according to the user account, and thus an algorithm suitable for each user may be provided.

For example, when there are different user accounts A and B using the electronic device 132 as shown in example view 750(*a*) of FIG. 7B, the user accounts A and B may include the same user pattern information or may include different user pattern information.

In an embodiment, when the user of the account A determines that the type of the detector of Protocol_5 is the stand type at step 720*c* of FIG. 7A, the user pattern information of the account A may set the type of the detector of the Protocol_5 to the stand type. On the other hand, when the user of the account B determines that the detector type of the Protocol_5 is the table type, the user pattern information of the account B may set the detector type of the Protocol_5 to the table type. In this case, even when one protocol list is received as shown in example view 750(*b*) of FIG. 7B, different orders of protocols may be generated according to the user accounts as shown in example view 750(*c*) of FIG. 7B. More specifically, the user pattern information of the account A classifies only Protocol_3 and 4 as the table type, whereas the user pattern information of the account B classifies the Protocol_5 as the table type in addition to the Protocol_3 and 4.

Figure 8A:
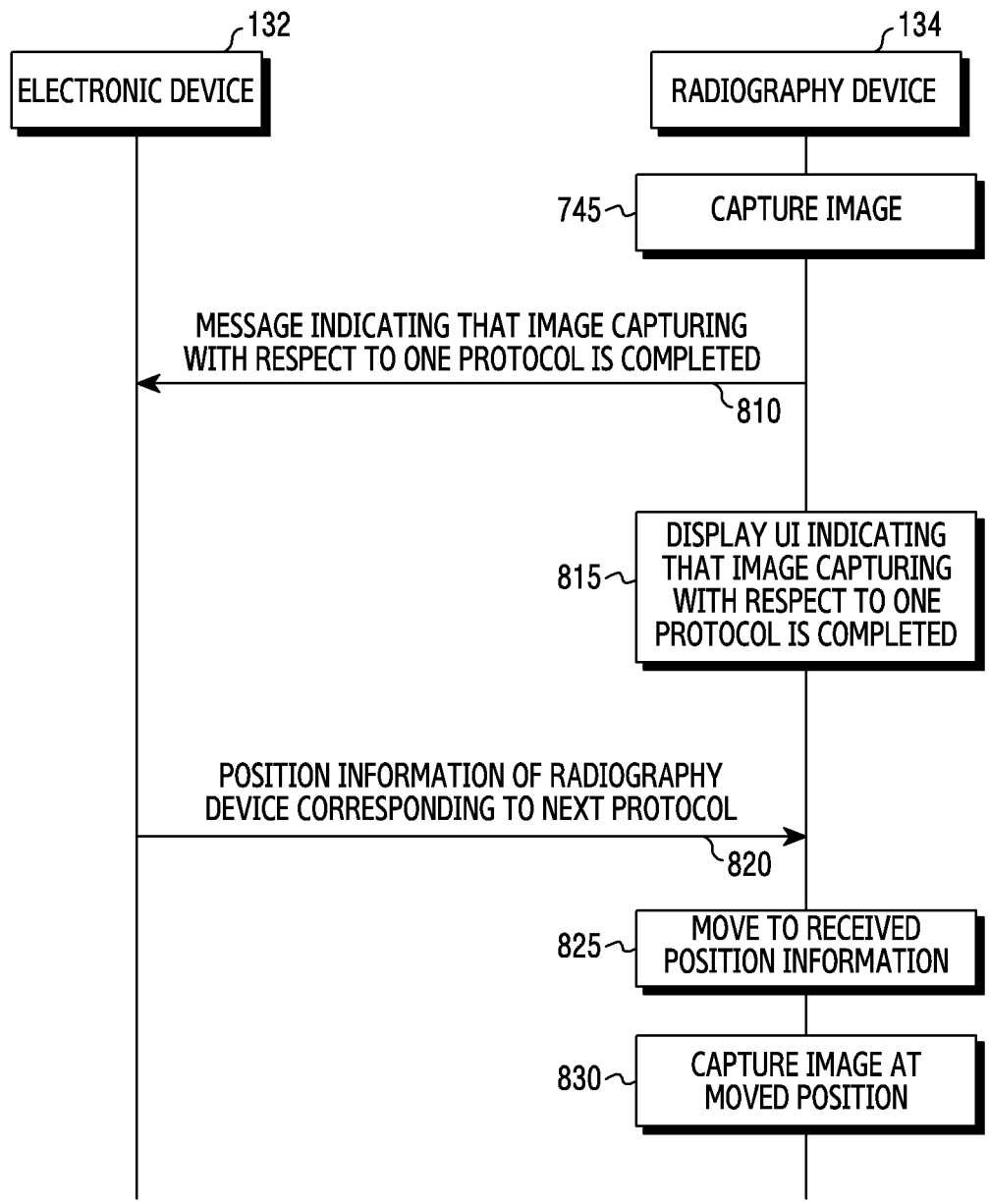

FIGS. 8A and 8B illustrate an example of an operation of automatically performing image capturing. FIG. 8A illustrates a signal flowchart for automatically performing image capturing according to various embodiments, and FIG. 8B illustrates an example of an operation of displaying a UI for a user to automatically perform image capturing.

Referring to FIG. 8A, when the radiography device 134 performs image capturing with respect to any one of the plurality of protocols at step 745, the radiography device 134 transmits, to the electronic device 132, a message indicating that the image capturing with respect to the protocol is completed at step 810. The message may include information regarding the protocol for which the image capturing is completed.

At step 815, the radiography device 134 displays a UI indicating that the image capturing with respect to the protocol is completed for the user through the input/output interface 322 included in the radiography device 815. For example, the radiography device 134 may directly display the UI indicating that image capturing with respect to a current protocol is completed, or may indirectly inform that the image capturing with respect to the current protocol is completed by displaying a UI indicating that image capturing with respect to a next protocol will be performed as shown in example view 840(*a*) of FIG. 8B. The user of the radiography device 134 may identify that the image capturing with respect to the protocol is completed through the displayed UI. When a predefined time comes without a separate input of the user, the radiography device 134 may perform the next operation, or may perform the next operation in response to a user input on the input/output interface 322 being detected (that is, when the user presses a "confirm" button displayed on the display) as shown in example view 840(*a*) of FIG. 8B.

At step 820, the radiography device 134 receives position information corresponding to the next protocol from the electronic device 132. The position information indicates a position where the radiography device 134 will perform image capturing with respect to the next protocol.

At step 825, the radiography device 134 moves to the received position information. For example, as shown in example view 840(*b*) of FIG. 8B, the radiography device 134 may automatically move to coordinate values indicated by the position information without control of the user.

At step 830, thee radiography device 134 performs image capturing with respect to the next protocol in the moved position. The operations of step 745 and steps 810 to 830 illustrated in FIG. 8A may be repeatedly performed to perform image capturing with respect to the next protocol. In addition, the radiography device 134 may display the list of protocols for which image capturing is completed for the user through the input/output interface 322 as shown in example view 840(*c*) of FIG. 8B although this operation is not illustrated in FIG. 8A.

FIG. 8A illustrates that the operations of the above-described steps are implemented according to the order, but the right scope of the disclosure is not limited to the above-described order. The operations of the above-described steps may be performed simultaneously or in different order. For example, the message indicating that image capturing with respect to the protocol is completed may be displayed before being transmitted.

In addition, according to an implementation method, the radiography device 134 may perform the operations of the above-described steps without exchanging data with the electronic device 132. For example, when the radiography device 134 receives the order of the protocols from the electronic device 132, the radiography device 134 may also receive position information regarding the protocols. In this case, the radiography device 134 may store the position information in the memory included in the radiography device 134. Thereafter, every time the image capturing with respect to each of the protocols is completed, the radiography device 134 may not receive the position information from the electronic device 132, and may move to an image capturing position for the next protocol based on the position information stored in the memory at step 825.

Figure 9A:
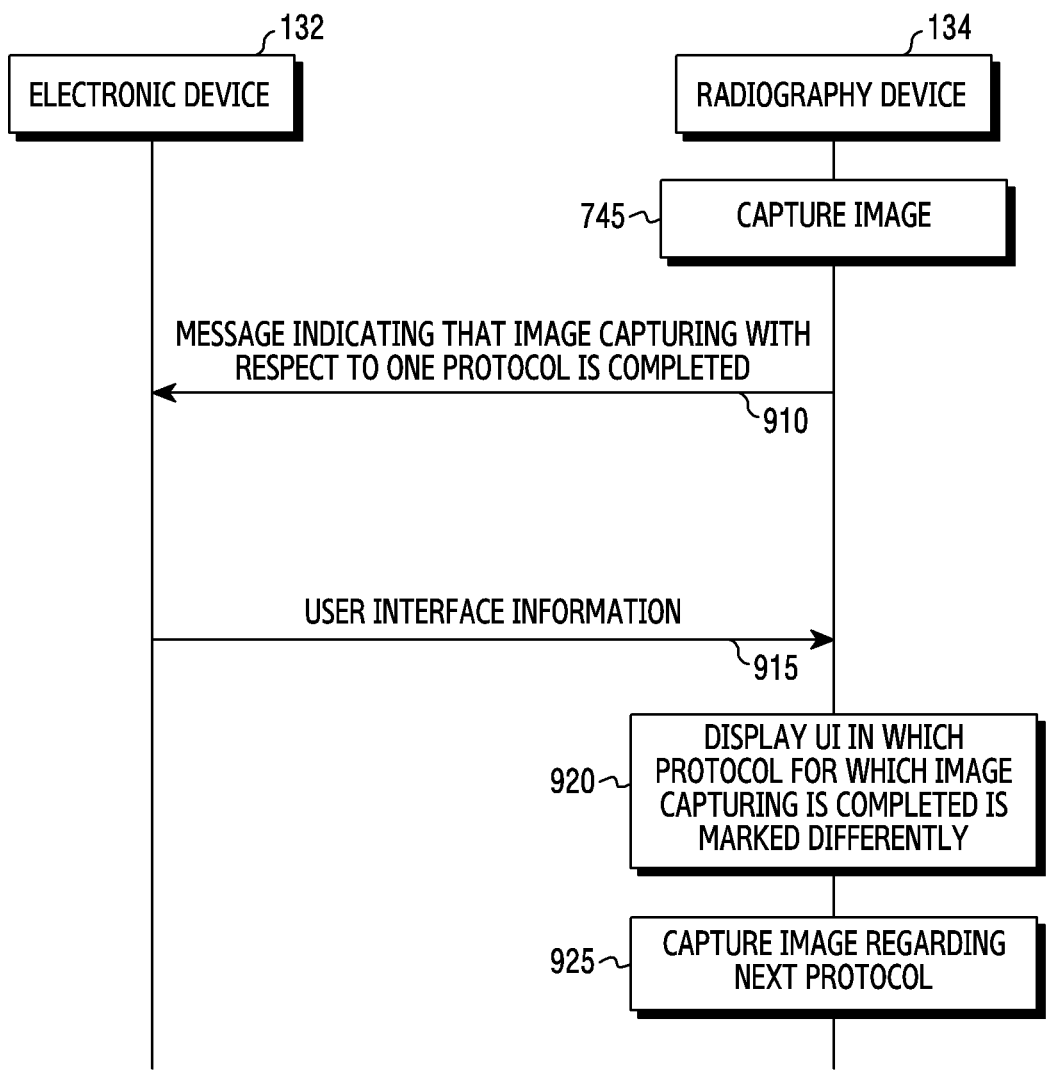
FIGS. 9A and 9B are views illustrating an example of an operation for displaying a list of protocols for which image capturing is completed for a user.
Figure 9B:
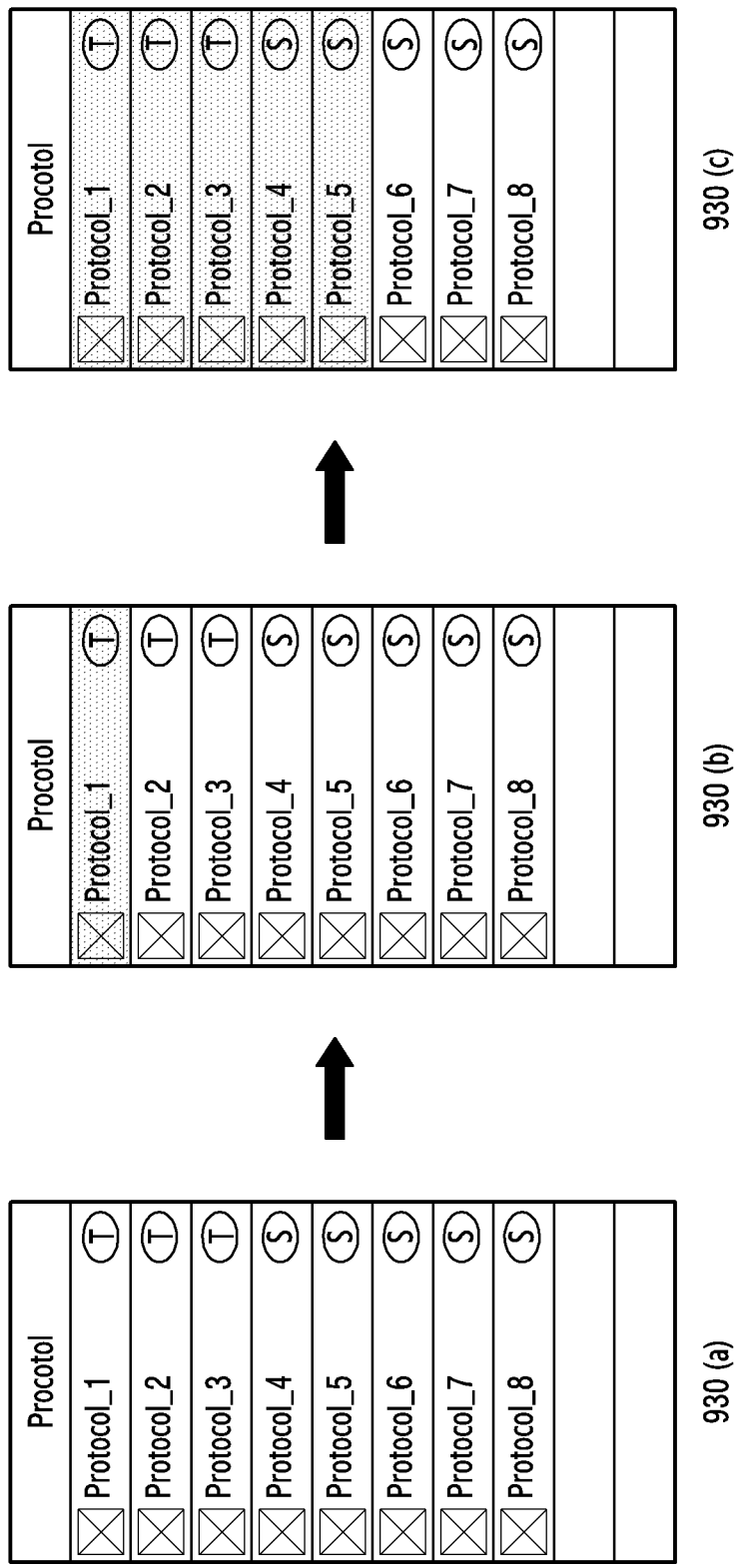

FIGS. 9A and 9B illustrate an example of an operation for displaying a list of protocols for which image capturing is completed for the user. FIG. 9A illustrates a signal flowchart for displaying the list of protocols for which image capturing is completed for the user according to various embodiments, and FIG. 9B illustrates an example of a UI displaying the protocols for which image capturing is completed.

Referring to FIG. 9A, the radiography device 134 performs image capturing with respect to one of the plurality of protocols at step 745. When it is assumed that image capturing with respect to the protocol is first image capturing, the radiography device 134 merely displays the protocols according to an image capturing order as shown in example view 930(*a*) of FIG. 9B.

At step 910, the radiography device 134 transmits a message indicating that the image capturing with respect to the protocol is completed to the electronic device 132. The message may include information regarding the protocol for which the image capturing is completed.

At step 915, the radiography device 134 receives UI information from the electronic device 132. The UI information may be information regarding a UI in which the protocol for which the image capturing is completed is differently marked from the other protocols.

At step 920, the radiography device 134 may output, to the user through the input/output interface 322, the UI in which the protocol for which the image capturing is completed is differently marked from the other protocols, based on the received UI information. For example, when image capturing with respect to Protocol_1 is completed, the radiography device 134 may display a UI in which only Protocol_1 is shaded as shown in example view 930(*b*) of FIG. 9B.

At step 925, the radiography device 134 performs image capturing with respect to the next protocol. The operations of step 745 and steps 910 to 930 illustrated in FIG. 9A may be repeatedly performed to perform image capturing with respect to the next protocol. For example, when the radiography device 134 performs image capturing up to Protocol_7, a display in which Protocol_1 to Protocol_5 are shaded may be displayed as shown in example view 9(c) of FIG. 9B. The user may identify the protocols for which image capturing is completed until the present time through the UI.

FIG. 9A illustrates that the operations of the above-described steps are implemented according to the order, but the right scope of the disclosure is not limited to the above-described order. The operations of the above-described steps may be performed simultaneously or in different order. In addition, according to an implementation method, the radiography device 134 may perform the operations of the next steps without exchanging data with the electronic device 132. For example, when the radiography device 134 receives the order of the protocols from the electronic device 132, the radiography device 134 may also receive information regarding the UI. In this case, the radiography device 134 may store the information regarding the UI in the memory included in the radiography device 134. Thereafter, the radiography device 134 may not receive the information regarding the UI from the electronic device 132 ever time image capturing with respect to each of the protocols is completed, and may display the UI shown in FIG. 9B based on the information regarding the UI stored in the memory at step 920.

As described above, the operation method of the electronic device in the radiography system may include: receiving, from the server, information regarding a first protocol list including a plurality of protocols; identifying position information of the radiography device which performs image capturing with respect to each of the plurality of protocols, and a type of a detector which detects a beam generated from the radiography device; generating a second protocol list by rearranging the order of the plurality of protocols, based on at least one of the position information of the radiography device and the type of the detector; and transmitting information regarding the second protocol list to the radiography device. The image capturing position information of the radiography device, and the type of the detector may be determined based on an image capturing technique indicated by each of the plurality of protocols.

In addition, the rearranging the order of the plurality of protocols may include: classifying the plurality of protocols into a first group and a second group, based on the type of the detector; rearranging an order of at least one protocol included in each of the first group and the second group, based on the position information of the radiography device; and rearranging the order of the at least one protocol rearranged in each of the first group and the second group, based on user pattern information. The user pattern information may correspond to each of a plurality of user accounts for accessing the electronic device, and may be determined based on at least one of the position information of the radiography device, the image capturing part information of the object, and the image capturing operation information of the object.

In addition, the operation method may further include: detecting an access to the electronic device by using at least one user account of the plurality of user accounts; receiving information regarding a detected user input from the radiography device; based on the information regarding the user input, generating a third protocol list by rearranging the order of the plurality of protocols included in the second protocol list; based on the generated third protocol list, refining the user pattern information corresponding to the user account; and storing the refined user pattern information.

In addition, the operation method may further include: receiving a fourth protocol list including a plurality of other protocols from the server; detecting an access to the electronic device by using the user account; generating a fifth protocol list by rearranging the plurality of other protocols based on the refined user pattern information; and transmitting information regarding the fifth protocol list to the radiography device.

In addition, the operation method may further include: receiving, from the radiography device, a message indicating that image capturing with respect to one of the plurality of protocols included in the second protocol list is completed; and transmitting, to the radiography device, position information of the radiography device corresponding to a next protocol.

In addition, the operation method may further include transmitting, to the radiography device, UI information in which the protocol for which the image capturing is completed is marked differently from the other protocols of the plurality of protocols.

As described above, the operation method of the radiography device in the radiography system may include: receiving information regarding a second protocol list from an electronic device; and, based on an order of a plurality of protocols included in the second protocol list, performing image capturing with respect to each of the plurality of protocols. The second protocol list may be generated by rearranging an order of the plurality of protocols included in a first protocol list, and may be generated based on at least one of position information of the radiography device regarding each of the plurality of protocols, and a type of a detector for detecting a beam generated from the radiography device. The image capturing position information of the radiography device, and the type of the detector may be determined based on an image capturing technique indicated by each of the plurality of protocols.

In addition, the second protocol list may be generated based on user pattern information stored in the electronic device, in addition to the position information and the type of the detector, and the user pattern information may correspond to each of a plurality of user accounts for accessing the electronic device, and may be determined based on at least one of position information of the radiography device, image capturing part information of the object, and image capturing operation information of the object. In addition, the user pattern information may be refined by the electronic device, based on information regarding a user input detected from the electronic device.

In addition, the operation method may further include: when image capturing with respect to one of the plurality of protocols is completed, displaying a UI indicating that the image capturing with respect to the protocol is completed; moving to an image capturing position regarding a protocol which is the next to the protocol from among the plurality of protocols included in the second protocol list; and performing image capturing with respect to the protocol corresponding to the next order at the moved image capturing position.

In addition, the operation method may further include, when image capturing with respect to one of the plurality of protocols is completed, displaying a UI in which the protocol for which the image capturing is completed is marked differently from the other protocols.

While specific embodiments have been described in the detailed description of the disclosure, it will be understood by those skilled in the art that various changes may be made therein without departing from the spirit and scope of the disclosure. Therefore, the scope of the disclosure should be defined not by the embodiments described above but by the appended claims or equivalents to the claims.

In addition, the embodiments disclosed in the disclosure and the drawings are suggested for easy explanation and understanding of the disclosed technical features, and are not intended to limit the scope of the disclosure. Therefore, the scope of the disclosure should be interpreted as including all changes or modified forms derived based on the technical idea of the disclosure, in addition to the embodiments disclosed herein.

What is claimed is:

1. An operation method of an electronic device in a radiography system, the method comprising:
  receiving, from a server, information regarding a first protocol list comprising a plurality of protocols;
  identifying position information of a radiography device which performs image capturing with respect to each of the plurality of protocols, and a type of a detector which detects a beam generated from the radiography device;
  generating a second protocol list by rearranging the order of the plurality of protocols, based on at least one of the position information of the radiography device and the type of the detector and based on user pattern information related to use of the radiography device;
  transmitting information regarding the second protocol list to the radiography device,
  receiving information on a user input from the radiography device in response to transmitting the information regarding the second protocol list;
  generating a third protocol list by rearranging the order of the plurality of protocols in the second protocol list based on the information on the user input; and
  transmitting information regarding the third protocol list to the radiography device,
  wherein the position information of the radiography device, and the type of the detector are determined based on an image capturing technique indicated by each of the plurality of protocols.

2. The method of claim 1, wherein the image capturing technique indicated by each of the plurality of protocols comprises at least one of image capturing part information of an object, a direction of the beam generated from the radiography device, and image capturing operation information of the object.

3. The method of claim 2, wherein generating the second protocol list rearranging the order of the plurality of protocols comprises:
  classifying the plurality of protocols into a first group and a second group, based on the type of the detector;
  rearranging an order of at least one protocol included in each of the first group and the second group, based on the position information of the radiography device; and
  rearranging the order of the at least one protocol rearranged in each of the first group and the second group, based on the user pattern information,
  wherein the user pattern information corresponds to each of a plurality of user accounts for accessing the electronic device,
  wherein the user pattern information is determined based on at least one of the position information of the radiography device, the image capturing part information of the object, and the image capturing operation information of the object.

4. The method of claim 3, further comprising:
  detecting an access to the electronic device by using at least one user account of the plurality of user accounts;
  refining the user pattern information corresponding to the user account based on the generated third protocol list; and
  storing the refined user pattern information.

5. The method of claim 2, further comprising:
  receiving, from the radiography device, a message indicating that image capturing with respect to one of the plurality of protocols included in the second protocol list is completed; and
  transmitting, to the radiography device, position information of the radiography device corresponding to a next protocol.

6. The method of claim 5, further comprising:
  transmitting, to the radiography device, UI information in which the protocol for which the image capturing is completed is marked differently from the other protocols of the plurality of protocols.

7. An electronic device in a radiography system, the electronic device comprising:
  a transceiver; and
  at least one processor functionally coupled to the transceiver,
  wherein the at least one processor is configured to:
  control to receive, from a server, information regarding a first protocol list comprising a plurality of protocols;
  identify position information of a radiography device which performs image capturing with respect to each of the plurality of protocols, and a type of a detector which detects a beam generated from the radiography device;
  generate a second protocol list by rearranging the order of the plurality of protocols, based on at least one of the position information of the radiography device and the type of the detector and based on user pattern information related to use of the radiography device;
  control to transmit information regarding the second protocol list to the radiography device,
  receiving information on a user input from the radiography device in response to transmitting the information regarding the second protocol list;
  generating a third protocol list by rearranging the order of the plurality of protocols in the second protocol list based on the information on the user input; and
  transmitting information regarding the third protocol list to the radiography device,
  wherein the position information of the radiography device, and the type of the detector are determined based on an image capturing technique indicated by each of the plurality of protocols.

8. The electronic device of claim 7, wherein the image capturing technique indicated by each of the plurality of protocols comprises at least one of image capturing part information of an object, a direction of the beam generated from the radiography device, and image capturing operation information of the object.

9. The electronic device of claim 8, wherein the at least one processor is further configured to:
  classify the plurality of protocols into a first group and a second group, based on the type of the detector;
  rearrange an order of at least one protocol included in each of the first group and the second group, based on the position information of the radiography device; and generate the second protocol list by rearranging the order of the at least one protocol rearranged in each of the first group and the second group, based on the user pattern information, wherein the user pattern information corresponds to each of a plurality of user accounts for accessing the electronic device, wherein the user pattern information is determined based on at least one of the position information of the radiography device, the image capturing part information of the object, and the image capturing operation information of the object.

10. The electronic device of claim 9, wherein the at least one processor is further configured to:
   detect an access to the electronic device by using at least one user account of the plurality of user accounts;
   refine the user pattern information corresponding to the user account based on the generated third protocol list; and
   store the refined user pattern information.

11. The electronic device of claim 9, wherein the user pattern information is refined by the electronic device, based on the generated third protocol list.

12. The electronic device of claim 8, wherein the at least one processor is further configured to:
   control to receive, from the radiography device, a message indicating that image capturing with respect to one of the plurality of protocols included in the second protocol list is completed, and
   control to transmit, to the radiography device, position information of the radiography device corresponding to a next protocol.

13. The electronic device of claim 12, wherein the at least one processor is further configured to transmit, to the radiography device, UL information in which the protocol for which the image capturing is completed is marked differently from the other protocols of the plurality of protocols.

14. The electronic device of claim 7,
   wherein the user patter information corresponds to each of a plurality of user accounts for accessing the electronic device, and determined based on at least one of position information of the radiography device, image capturing part information of the object, and image capturing operation information of the object.

* * * * *